(12) United States Patent
Harkins, Jr. et al.

(10) Patent No.: US 8,119,846 B2
(45) Date of Patent: Feb. 21, 2012

(54) SEPARATION AND/OR RECOVERY OF PROPYL BROMIDE

(75) Inventors: Alvin E. Harkins, Jr., Baton Rouge, LA (US); James E. Torres, Clinton, LA (US); Keith G. Anderson, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 693 days.

(21) Appl. No.: 12/299,887

(22) PCT Filed: Jun. 1, 2007

(86) PCT No.: PCT/US2007/070168
§ 371 (c)(1),
(2), (4) Date: Nov. 6, 2008

(87) PCT Pub. No.: WO2007/143519
PCT Pub. Date: Dec. 13, 2007

(65) Prior Publication Data
US 2009/0240091 A1    Sep. 24, 2009

Related U.S. Application Data

(60) Provisional application No. 60/803,833, filed on Jun. 2, 2006.

(51) Int. Cl.
*C07C 17/38* (2006.01)
(52) U.S. Cl. ...................................................... 570/262
(58) Field of Classification Search ........................ None
See application file for complete search history.

(56) References Cited

U.S. PATENT DOCUMENTS

| 2,307,552 | A |   | 1/1943 | Vaughan et al. |
|---|---|---|---|---|
| 2,499,629 | A | * | 3/1950 | Calfee et al. ............. 204/158.11 |
| 2,672,439 | A |   | 3/1954 | Den Hertog et al. |
| 3,372,207 | A | * | 3/1968 | Hutson, Jr. ..................... 585/314 |
| 3,522,172 | A | * | 7/1970 | Hahn et al. ..................... 210/635 |
| 2005/0065386 | A1 |   | 3/2005 | Meirom et al. |
| 2008/0058554 | A1 |   | 3/2008 | Anderson et al. |

FOREIGN PATENT DOCUMENTS

| WO | 03042138 A1 | 5/2003 |
|---|---|---|
| WO | 2006113307 A1 | 10/2006 |
| WO | 2007121228 A2 | 10/2007 |

* cited by examiner

*Primary Examiner* — Daniel Sullivan
*Assistant Examiner* — Clinton Brooks
(74) *Attorney, Agent, or Firm* — Marcy M. Hoefling; Jeremy J. Kliebert; James A. Jubinsky

(57) ABSTRACT

Described is a process for separating an organic phase comprising mainly propyl bromide from a crude reaction mixture formed by free-radical catalyzed hydrobromination of propylene with hydrogen bromide. The process comprises (A) feeding cold water into an upper or mid-portion of a packed column; (B) concurrently feeding the crude reaction mixture into an upper portion and/or mid-portion of the column so that the water contacts the crude reaction mixture; to form a mixture of (i) an acidic aqueous phase comprising aqueous hydrogen bromide and (ii) an organic phase comprising propyl bromide; (C) withdrawing the resultant phases from said column, at a rate comparable to the feeds being made into the column; and (D) separating the phases to form an upper acidic aqueous phase comprising aqueous hydrogen bromide superposed on a lower liquid organic phase comprising propyl bromide, and separating these upper and lower phases from each other.

15 Claims, 1 Drawing Sheet

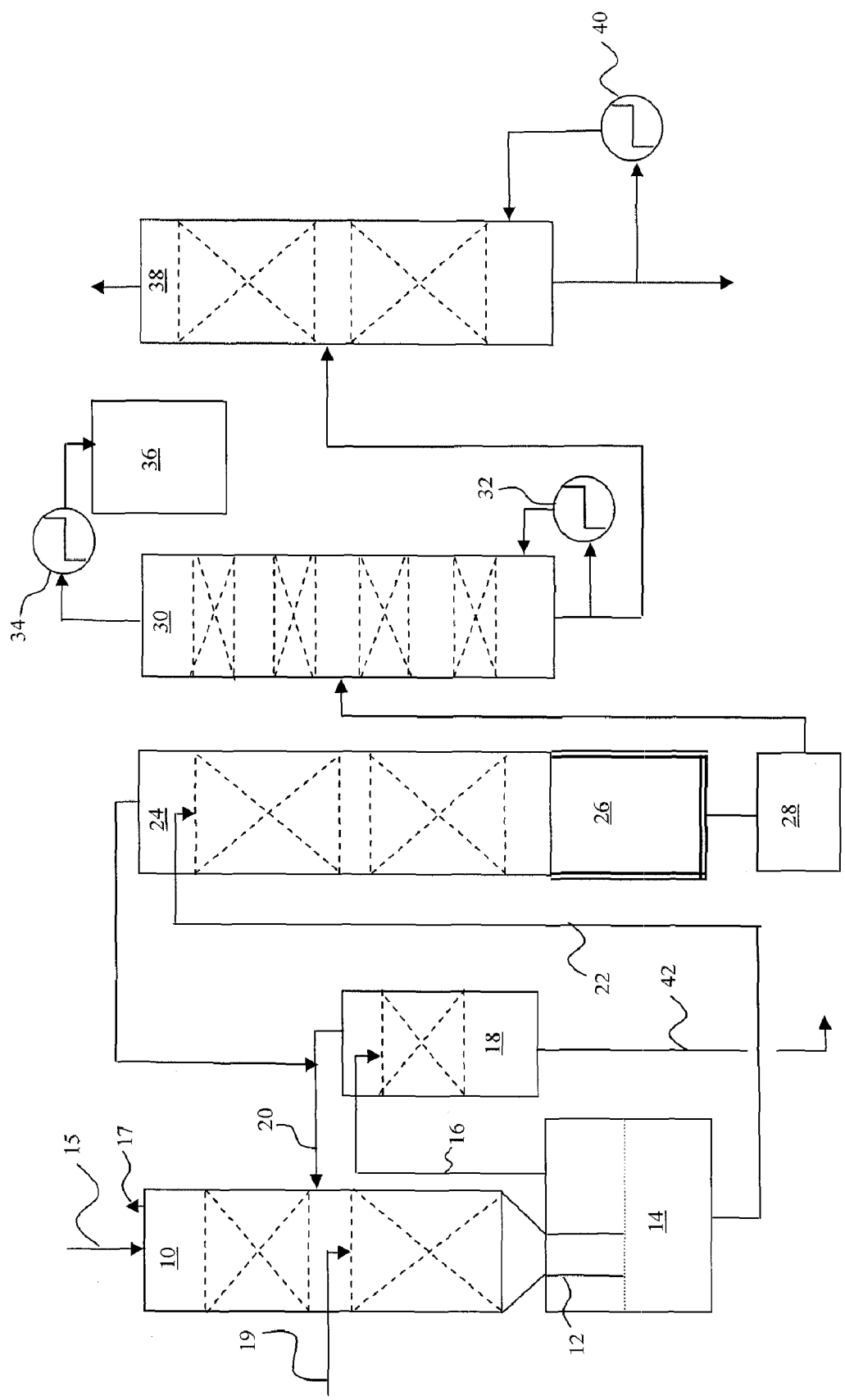

SEPARATION AND/OR RECOVERY OF PROPYL BROMIDE

REFERENCE TO RELATED APPLICATIONS

This application is the National Stage of International Patent Application PCT/US2007/070168, filed on Jun. 1, 2007, which application claims priority from U.S. Application No. 60/803,833, filed Jun. 2, 2006, the disclosures of which are incorporated herein by reference.

BACKGROUND

The two isomers of propyl bromide (n-propyl bromide or "NPB") and isopropyl bromide or "IPB") are both commercially useful products. NPB is the more widely used of the two. It is desirable to provide them in as high purities as possible.

Methods for producing propyl bromide (i.e., both of NPB and IPB with the amount of NPB predominating over IPB) are known. One such general method involves hydrobromination of propylene using free-radical catalysis. Commonly-owned copending applications (Cases B1-7282 PCT, filed Apr. 13, 2006 with a priority date of Apr. 18, 2005; and B1-7448, filed Apr. 13, 2006) describe preferred hydrobromination reactions of this type. For example, the process of B1-7448 as applied to propyl bromide production comprises continuously feeding propylene, gaseous hydrogen bromide, and a molecular oxygen-containing gas into a liquid phase reaction medium comprised of aliphatic bromide (preferably propyl bromide corresponding to that being produced) to cause anti-Markovnikov addition of HBr to propylene, the feeds being proportioned and maintained to provide a molar excess of hydrogen bromide relative to propylene in the range of about 1 to about 5 percent, and a molar ratio of molecular oxygen to propylene of less than 0.005, and preferably in the range of about 0.00005:1 to about 0.001:1. The principal product is NPB with small amounts of IPB also being co-formed.

Studies in our laboratories have shown that formation of trace amounts of bromine and peroxy radicals are formed during the hydrobromination reaction. This in turn leads to the formation of small amounts of various other by-products such as 1,2-dibromopropane, acetone, bromoacetone, propionaldehyde, 1,3-dibromoacetone, 1-propanol, and 2-propanol. The formation of acetone and bromoacetone, typically at levels of about 200 ppm, is especially undesirable as bromoacetone even at such low concentrations is a powerful lachrymator. Also when it is desired to recover isopropyl bromide as a co-product, acetone is troublesome as it has a boiling point essentially the same as the boiling point of isopropyl bromide and thus is very difficult to separate these materials from each other.

Conventional distillation procedures can be used to purify propyl bromide products (NPB and IPB) formed by the hydrobromination of propylene. However, such distillations typically require expensive distillation facilities operated under close control of conditions if highly pure NPB, and optionally highly pure IBP, are to be recovered.

BRIEF SUMMARY OF THE INVENTION

Pursuant to this invention the propylene hydrobromination reaction mixture is subjected to treatment with a flow of cold water in a packed column to produce two intermixed or interspersed phases which are removed and allowed to coalesce, and are then separated from each other. Such treatment enables subsequent operations to be conducted whereby exceptionally pure NPB and IBP can be separated and individually recovered.

Accordingly, one embodiment of this invention is a process for separating an organic phase comprising mainly propyl bromide from a crude reaction mixture formed by free-radical catalyzed hydrobromination of propylene with hydrogen bromide, which process comprises:
A) feeding cold water into an upper or mid portion of a packed column having an upper portion, a mid-portion, and a lower portion;
B) concurrently feeding said crude reaction mixture into an upper portion and/or mid-portion of said column so that the water contacts the crude reaction mixture to form a mixture of an acidic aqueous phase comprising aqueous hydrogen bromide and an organic phase comprising propyl bromide;
C) withdrawing said phases from said column, preferably from the lower portion, and still more preferably from the bottom, of the packed column at a rate comparable to the feeds being made into said column in A) and B); and
D) separating said phases, typically in a separate vessel, to form an upper acidic aqueous phase comprising aqueous hydrogen bromide superposed on a lower liquid organic phase comprising propyl bromide, and separating these upper and lower phases from each other.

In A) the cold or chilled water is preferably fed into an upper portion of the packed column and in B) the crude mixture is preferably fed into the column at a locus below the feed of the cold water in A). It is further preferred that the lower portion of the packed column contain in addition to packing, a semi static aqueous phase through which liquid organic phase comprising propyl bromide falls. From this lower portion, a combination or mixture of acidic aqueous phase comprising hydrogen bromide and organic phase comprising propyl bromide flow into a vessel for separation into two distinct phases, viz., the upper acidic phase and the lower liquid organic phase. The fact that the water has absorbed the HBr and is thus acidic is highly advantageous in that the presence of the acid in the water accelerates the rate at which the distinct separate organic and acidic aqueous phases are formed in the separate vessel.

In addition to aqueous hydrogen bromide (dilute hydrobromic acid), the upper acidic aqueous phase typically contains entrained and/or dissolved propyl bromide, and may contain as much as about 3500 ppm (wt/wt) of propyl bromide. If the initial HBr used in the hydrobromination contains some HCl, the upper acidic aqueous phase will contain this as well. Usually HBr containing HCl impurity used in the hydrobromination will contain less than about 5% of the HCl. The lower liquid organic phase comprising propyl bromides typically also contains small amounts of organic co-products and/or impurities and some entrained and/or dissolved water and/or aqueous acid. Typically, the amount of such aqueous content will be up to about 500 ppm (wt/wt).

It will be noted that the packed column serves multiple functions including absorption, condensation, and coalescing. Various types of acid resistant packing materials can be used in the above packed column. Thus, packing materials that can be used include Raschig rings, plastic random packing, or structured plastic packing. Such materials are readily available from various commercial sources.

There are various operational steps and sequences that can be used in processing the separated phases from D). Preferred steps and sequences of this type are described in detail herein, and involve various additional embodiments of this invention. Therefore the above and other steps, sequences, and embodiments will become still further apparent from the ensuing description, appended claims, and accompanying drawings.

Among the advantages of this invention is the fact that the entire process can be carried out on a continuous basis. This in turn enables use of smaller, less expensive reaction equipment in a plant facility.

BRIEF DESCRIPTION OF THE DRAWING

FIG. 1 is a schematic flow diagram illustrating various operational steps and sequences in a preferred overall sequence of operations of this invention, such steps, sequences, and overall sequence constituting, respectively, individual embodiments of this invention.

FURTHER DETAILED DESCRIPTION OF EMBODIMENTS OF THIS INVENTION

As used herein including the claims, and unless expressly indicated otherwise:

the terms "propyl bromide" and "PBr" refer to a combination or mixture of n-propyl bromide (NPB) and isopropyl bromide (IPB) in which at least 70%, and typically at least 90% or more of these two components is n-propyl bromide (NPB).

the terms "crude propyl bromide" and "crude PBr" refer to propyl bromide, PBr, in admixture with co-products and/or impurities resulting from preparation by hydrobromination of propylene with hydrogen bromide which optionally contains a small percentage of hydrogen chloride (typically no more than about 5 wt % of the mixture of HBr and HCl) in the presence of molecular oxygen.

I. Typical Hydrobromination Reaction

Crude PBr is produced in a hydrobromination reactor. The reactor is typically cooled by indirect heat exchange with refrigerated glycol/water. Propylene, HBr, and a free-radical catalyst such as a peroxide catalyst, molecular oxygen, or air are typically fed to the reactor. In a preferred operation, a very small amount of molecular oxygen or air is used as catalyst, and the propylene, HBr, and the small amount of catalyst are fed subsurface to a heel of PBr liquid at 40° F. (ca. 4.5° C.). Use of such small amounts of molecular oxygen or air as catalyst in such hydrobromination reactions is described in more detail in commonly-owned copending application (B1-7448) the disclosure of which is incorporated herein. The reactor is run "buttoned up" (no vent) at a vapor pressure of 10-15 psig. Crude PBr liquid is removed from the reactor.

II. Steps and Sequences of One Overall Sequence of this Invention

Referring now to the steps and sequences depicted in FIG. 1, crude PBr is fed via line 19 into packed column 10, preferably into a mid-portion of the column between two packed sections (an upper section and a lower section). Chilled water (typically in the range of about 50 to about 60° F.) is fed to the top of packed column 10 via line 15 for direct contact with crude PBr in the column. An atmospheric vapor vent 17 at the top of column 10 is the only permitted vent point for the front-end of the overall process. This vent point enables propane (and when air is used as the catalyst in the hydrobromination, nitrogen and inert gases that were present in the air) to exit from the otherwise sealed system. Chilled water absorbs excess HBr (and HCl contained in HBr) and becomes dilute acidic "aqueous" for reuse. The free space in the lower packed section of column 10 is filled by a semi-static aqueous liquid phase. PBr in an organic phase flows as a separate liquid phase through the aqueous phase and both phases exit from a lower portion of column 10 via line 12. It will be seen that column 10 serves in several capacities, viz., as an absorber/condenser/coalescing column.

Both phases in line 12 enter vessel 14, preferably disposed under column 10. The two phases separate in vessel 14 which is hydraulically full with a two-phase mix: organic phase with PBr on the bottom and the aqueous phase on top. Preferably the phase interface level is maintained in the middle of vessel 14.

Aqueous phase containing at least about 3000 ppm (typically saturated with PBr at ~3,500 ppm) exits from the top of vessel 14 via line 16 to steam stripper column 18. Steam (e.g., at 60 psig/307° F.) (ca. 153° C.) is directly injected into the bottom of stripper column 18 to heat the aqueous phase and strip out organic phase containing PBr which leaves via line 20. Column 18 overhead vapor (steam and stripped organic) is fed back into packed column 10 for condensation.

"Wet" crude PBr (typically saturated with aqueous phase at ~500 ppm) exits from the bottom portion of vessel 14, and is transmitted via line 22 as feed to dryer column 24. Disposed under dryer column 24 is jacketed reboiler drum 26. Steam (e.g., at 60 psig/307° F.) (ca. 153° C.) is fed to the jacket of drum 26 to boil the PBr contained within dryer column 24. The boiling PBr travels up dryer column 24 and strips (dries) the aqueous that entered with the feed. C-5620 overhead vapor from dryer column 24 (mainly PBr/H2O/HBr, and HCl if present in the original HBr) is fed back into packed column 10C-5610 for condensation. Bottoms from dryer column 24 (dry crude PBr, typically at <1 ppm water) is pumped to a storage vessel 28 for storage at a rate that maintains a constant level in dryer column 24.

Dry crude PBr from vessel 28 is fed to splitter column 30 below which is connected reboiler 32. Column 30 separates pure IPB overhead and NPB/heavies out the bottom. Steam (e.g., at 60 psig/307° F.) (ca. 153° C.) feeds reboiler 32 to supply boil-up heat to column 30. Pure IPB (overhead) condenses in water-cooled overhead exchanger 34 disposed above and connected with column 30 and flows to rundown tank 36 for storage. If desired, more than one such tank can be used. In such case one tank can be filled while the product in another tank is circulated or mixed, sampled for quality, and then offloaded.

NPB heavies, bottoms from splitter column 30, feed column 38. Column 38 separates pure NPB overhead. The heavies (coproducts and any other remaining impurities, e.g., dibromopropane, bromoacetone, dibromoacetone, etc.) accumulate in the bottom of column 38. The heavies are diluted with a portion of NPB. Again, steam e.g., at 60 psig/307° F.) (ca. 153° C.) feeds a reboiler 40 to supply boil-up heat to column 38.

In this overall sequence of operations there is no need for continuous bottom takeoff of heavies from column 38. The level in the bottom sump will slowly increase (concentrating the low levels of impurities formed in the front-end reaction process). When an appreciable level accumulates, a portion of the bottoms can be fed to a 55-gal waste drum for disposal. The bottoms stream typically will flow through a water-cooled heat exchanger prior to filling the waste drum.

If desired, stabilizers and/or other additives may be added to the recovered IPB and/or NPB.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what preliminary chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

The invention claimed is:

1. A process for separating an organic phase comprising mainly propyl bromide from a crude reaction mixture formed by free-radical catalyzed hydrobromination of propylene with hydrogen bromide, which process comprises:
   A) feeding cold water into an upper or mid-portion of a packed column having an upper portion, a mid-portion, and a lower portion;
   B) concurrently feeding said crude reaction mixture into an upper portion and/or mid-portion of said packed column so that the water contacts the crude reaction mixture to form a mixture of (i) an acidic aqueous phase comprising aqueous hydrogen bromide and (ii) an organic phase comprising propyl bromide;
   C) withdrawing said phases from said packed column, at a rate comparable to the feeds being made into said packed column in A) and B);
   D) separating said phases to form an upper acidic aqueous phase comprising aqueous hydrogen bromide superposed on a lower liquid organic phase comprising propyl bromide, and separating these upper and lower phases from each other, wherein the separated organic phase also contains entrained and/or dissolved aqueous phase;
   E) feeding the separated organic phase into a dryer column to strip aqueous phase from dried crude organic phase comprising propyl bromide;
   F) recovering the dried crude organic phase comprising propyl bromide as bottoms from the dryer column; and
   G) feeding the recovered bottoms from the dryer column to a splitter column, wherein isopropyl bromide is distilled from the bottoms as overhead and the overhead is recovered.

2. A process as in claim 1 wherein in A) the cold water is fed into an upper portion of the packed column and wherein in B) the crude mixture is fed into the packed column at a locus below the feed of the cold water in A).

3. A process as in claim 2 wherein said locus is in said mid-portion of said packed column.

4. A process as in claim 1 wherein said lower portion of said packed column contains in addition to packing, a semi static aqueous phase through which liquid organic phase comprising propyl bromide falls, and wherein a combination or mixture of (i) acidic aqueous phase comprising hydrogen bromide and (ii) organic phase comprising propyl bromide flow into a vessel for separation in D).

5. A process as in claim 1 wherein the packing in said packed column is Raschig rings.

6. A process as in claim 1 wherein the packing in said packed column is plastic random packing.

7. A process as in claim 1 wherein the packing in said packed column is structured plastic packing.

8. A process as in claim 4 wherein said phases (i) and (ii) flow from the lower portion of said packed column into said separate vessel.

9. A process as in claim 4 wherein said phases (i) and (ii) flow from the bottom of said packed column and into said separate vessel.

10. A process as in claim 1 wherein said lower portion of the packed column contains in addition to packing, a semi-static aqueous phase, wherein said cold water is fed into an upper portion of the packed column, wherein said crude mixture is fed into said packed column at a locus below said feed of cold water, wherein both acidic water containing HBr and organic phase comprising propyl bromide pass into said semi-static aqueous phase, and wherein a mixture of water containing HBr and organic phase comprising propyl bromide are withdrawn from the bottom of said packed column for phase separation in D).

11. A process as in claim 1 wherein the aqueous phase separated in D) contains entrained and/or dissolved organic phase comprising propyl bromide, and such aqueous phase is fed into a stripper column to steam strip organic phase including propyl bromide from the aqueous phase.

12. A process as in claim 1 wherein the aqueous phase stripped from said dryer column is fed into the packed column in A).

13. A process as in claim 1 wherein recovered bottoms from said splitter column comprising mainly n-propyl bromide together with organic coproducts and/or impurities, are recovered for purification.

14. A process as in claim 13 wherein the recovered bottoms from said splitter column are subjected to distillation to separate and recover purified n-propyl bromide as distillation overhead.

15. A process for separating an organic phase comprising mainly propyl bromide from a crude reaction mixture formed by free-radical catalyzed hydrobromination of propylene with hydrogen bromide, which process comprises:
   A) feeding cold water into an upper or mid-portion of a packed column having an upper portion, a mid-portion, and a lower portion;
   B) concurrently feeding said crude reaction mixture into an upper portion and/or mid-portion of said packed column so that the water contacts the crude reaction mixture to form a mixture of (i) an acidic aqueous phase comprising aqueous hydrogen bromide and (ii) an organic phase comprising propyl bromide;

C) withdrawing said phases from said packed column, at a rate comparable to the feeds being made into said packed column in A) and B);

D) separating said phases to form an upper acidic aqueous phase comprising aqueous hydrogen bromide superposed on a lower liquid organic phase comprising propyl bromide, and separating these upper and lower phases from each other, wherein the separated organic phase also contains entrained and/or dissolved aqueous phase;

E) feeding the separated organic phase into a dryer column to strip aqueous phase from dried crude organic phase comprising propyl bromide; and F) feeding the aqueous phase stripped from the dryer column into the packed column in A).

* * * * *